United States Patent [19]

Boross et al.

[11] Patent Number: 4,556,637

[45] Date of Patent: Dec. 3, 1985

[54] IMMOBILIZED CHOLINESTERASE ENZYME PREPARATIONS AND A PROCESS FOR THE PREPARATION THEREOF

[75] Inventors: László Boross; Béla Szajáni; Kamilla Kovacs, all of Budapest, Hungary

[73] Assignee: Reanal Finomvegyszergyar, Budapest, Hungary

[21] Appl. No.: 486,286

[22] PCT Filed: Dec. 23, 1981

[86] PCT No.: PCT/HU81/00047

§ 371 Date: Mar. 8, 1983

§ 102(e) Date: Mar. 8, 1983

[87] PCT Pub. No.: WO83/00345

PCT Pub. Date: Feb. 3, 1983

[30] Foreign Application Priority Data

Jul. 17, 1981 [HU] Hungary ................................ 2088/81

[51] Int. Cl.$^4$ ........................ C12N 11/06; C12N 11/08
[52] U.S. Cl. ...................................... 435/181; 435/180
[58] Field of Search ............................... 435/180, 181

[56] References Cited

U.S. PATENT DOCUMENTS 4,332,694  6/1982  Kalal ..................................... 435/180

OTHER PUBLICATIONS

Li et al., Chem. Abst., vol. 97 (1982), p. 18737h.
Aizenberg et al., Chem. Abst., vol. 97 (1982), p. 213278r.

Primary Examiner—Sam Rosen
Attorney, Agent, or Firm—Young & Thompson

[57] ABSTRACT

Immobilized cholinesterase enzyme preparations are prepared by treating a polymeric resin, built up from acrylic acid and/or methacrylic acid and acryl amide and/or methacryl amide monomers with an acryl or allyl type cross-linking agent and containing at least 0.1 meq/g of —COOH functional groups, with a carbodiimide derivative which is soluble in water or is soluble in an organic solvent at temperatures below 0° C., applying a solution of cholinesterase enzyme with a pH of 4.5 to 8.5 to the resulting activated support, washing the resulting product, and drying it if desired.

8 Claims, No Drawings

IMMOBILIZED CHOLINESTERASE ENZYME PREPARATIONS AND A PROCESS FOR THE PREPARATION THEREOF

The invention relates to new immobilized cholinesterase enzyme preparations as well as to a process for the preparation thereof.

It is known that cholinesterase enzyme, isolated most frequently from horse serum, can be applied to detect neurotoxins of phosphate ester, carbamate and sulfate ester type, and to determine the quantity of neurotoxins occurring in air or water. The basis of detection and measurement is the inhibiting effect exerted on the enzyme by neurotoxins. Thus, immobilized cholinesterase enzyme preparations may play the central role of continuously operating measuring systems. The principles of such measuring systems are described, among others, in Anal. Chem. 37, 1378 (1965) and Anal. Biochem. 51, 362 (1973).

Several methods have been described in the literature for the immobilization of cholinesterase isolated from horse serum. According to Anal. Chem. 37, 1378 (1965), Anal. Biochem. 19, 587 (1967), Anal. Biochem. 33, 341 (1970) and U.S. Pat. No. 3,223,593 the enzyme is entrapped in various gels, primarily starch gels. U.S. Pat. No. 3,223,593 also discloses the entrapment of the enzyme in agar and carrageen gels. The use of polyacrylamide as entrapping medium is suggested in Biochim. Biophys. Acta 212, 362 (1970) and Anal. Biochem. 33, 341 (1970). The enzyme can also be coupled through covalent bonds to polymeric macromolecules with appropriate functional groups. Thus e.g. according to Biochim. Biophys. Acta 191, 478 (1969) the enzyme is immobilized on Sepharose 2B activated previously with cyanogen bromide, whereas according to Biochim. Biophys. Acta 377, 297 (1975) polymaleic anhydride is applied as support. According to Clin. Chim. Acta 121, 125 (1980) the enzyme is immobilized on non-porous glass by carbodiimide or glutaric aldehyde coupling, whereas according to the USSR patent specification No. 707,923 the enzyme is coupled to porous glass or silica gel activated with cyanuric acid chloride. As described in Can. J. Biochem. 48, 1314 (1970), cholinesterase isolated from horse serum can also be attached to a Procion brilliant orange DEAE-cellulose complex through covalent bonds.

A disadvantage of the known cholinesterase enzyme preparations in which the enzyme is entrapped in a gel is that the enzyme dissolves continuously from it. Therefore, such preparations are not suitable for continuous, prolonged application. The known cholinesterase enzyme preparations immobilized on the substrate by covalent bonds have adverse throughflow properties from the aspects of application in automatic systems, moreover some of the supports, such as Sepharose 2B, are sensitive to microbial effects.

The invention aims at the elimination of the above disadvantages. According to the invention immobilized cholinesterase enzyme preparations are provided which meet the requirements of prolonged use, and contain the enzyme bound to a chemically and microbially inert support with appropriate mechanical properties ensuring a high throughflow rate. As a further advantage, the enzyme can be coupled to the support under mild reaction conditions.

It has been observed that polymeric resins built up from acrylic acid and/or methacrylic acid and acryl amide and/or methacryl amide monomers with acryl or allyl type cross-linking agents [such as N,N'-methylene-bis(acrylamide), ethylene diacrylate or N,N'-diallyl-tartaric amide], containing at least 0.1 meq/g, preferably 2 to 8 meq/g, of —COOH functional groups, completely meet the requirements set forth in connection with the supports. These supports can be prepared by methods known per se. One can proceed e.g. so that acryl amide and/or methacryl amide is copolymerized with acrylic acid and/or methacrylic acid in the presence of a cross-linking monomer, whereas according to another possible method a cross-linked polymer is prepared first from acryl amide and/or methacryl amide using the above cross-linking agents, and the acid amide groups of the resulting polymer are subjected then to partial hydrolysis to provide the required amount of —COOH functional groups. Akrilex C type enzyme supports, marketed by Reanal Finomvegyszergyár (Budapest, Hungary), prepared by subjecting Akrilex P type acryl amide —N,N'-methylene-bis(acrylamide)copolymer beads (e.g. Akrilex P-30, P-100 or P-200) to partial hydrolysis with an acid (e.g. hydrochloric acid or another strong acid) or a base (e.g. sodium hydroxide, sodium carbonate or another strong base), belong to this latter type of support polymers. In these substances about 50% of the —CONH$_2$ functional groups present are converted into carboxy groups upon hydrolysis, whereas the remaining —CONH$_2$ groups do not hydrolyze even under severe reaction conditions. Consequently, unchanged —CONH$_2$ groups are situated between the carboxy groups of the hydrolyzed copolymer, which fix the carboxy groups in favourable steric positions. If an enzyme is coupled to the carboxy groups by a carbodiimide activation method known per se, the functions of the individual immobilized enzyme molecules do not interfere with each other due to the favourable steric positions of the carboxy groups; thus the immobilized enzyme preparation may have a very high specific activity. Polymers containing acrylic acid and/or methacrylic acid and acryl amide and/or methacryl amide monomers connected to each other through a bifunctional cross-linking monomer and carrying at least 0.1 meq/g of —COOH functional groups, prepared by other methods, possess similar advantageous properties. These polymers have bead shape, thus they enable a great throughflow rate, and at the same time they are chemically inert and completely resistant to the effects of microorganisms.

The carboxy functional groups of these supports can be activated by the well-known carbodiimide method, and the resulting activated supports can bind cholinesterase enzyme. This reaction can be performed even under mild conditions (at temperatures of 0°–4° C. in a medium of pH~7.0).

Based on the above, the invention relates to immobilized cholinesterase enzyme preparations which contain the cholinesterase enzyme bound to a polymeric resin, built up from acrylic acid and/or methacrylic acid and acryl amide and/or methacryl amide monomers with acryl or allyl type cross-linking agents, containing at least 0.1 meq/g of —COOH functional groups, previously activated with a carbodiimide.

The invention also relates to a process for the preparation of these immobilized enzyme preparations. According to the invention a polymeric resin, built up from acrylic acid and/or methacrylic acid and acryl amide and/or methacryl amide monomers with an acryl or allyl type cross-linking agent and containing at least 0.1 meq/g of —COOH functional groups, is treated with a carbodiimide derivative which is soluble in water or is soluble in an organic solvent at a temperature below 0° C., a solution of cholinesterase enzyme with a pH of 4.5 to 8.5 is applied to the resulting activated support, the resulting product is washed, and then dried, if desired.

Akrilex C type polymers discussed above can be applied to particular advantage as supports for the cholinesterase enzyme.

Cholinesterase of any origin, isolated by any method, can be applied as enzyme in the process according to the invention.

To activate the polymeric support, e.g. N-cyclohexyl-N'-[β-(N-methylmorpholino)-ethyl]-carbodiimide p-toluenesulfonate or N-ethyl-N'-(3-dimethylaminopropyl)carbodiimide hydrochloride can be applied as carbodiimide derivative. It is preferred to utilize water-soluble carbodiimides for this purpose. Of the carbodiimide derivatives soluble only in organic solvents those substances can be applied in the process of the invention which have appropriate solubility in the given organic solvent even at low temperatures, i.e. below 0° C.

Cholinesterase is applied to the activated support from a solution of pH 4.5 to 8.5, preferably from an almost neutral solution (pH about 7.0). Cholinesterase is applied preferably as a solution formed with a 0.1 molar potassium phosphate buffer (pH=7.0).

The immobilized enzyme preparation formed in this coupling reaction is washed in a manner known per se, and then dried, if desired. The enzyme preparation is, however, also storable in aqueous suspensions at 0° to 4° C.

The specific activity of the immobilized enzyme preparations according to the invention is 100–120 units/1 g of xerogel, which, when compared to the activity data disclosed in Anal. Chem. 37, 1378 (1965), Anal. Biochem. 19, 587 (1967), Biochim. Biophys. Acta 212, 362 (1970) and Anal. Biochem. 51, 362 (1973), is favourable for practical use.

The immobilized enzyme preparations according to the invention are more stable in slightly alkaline media, i.e. at the optimum pH of their application (pH 8.0), than the soluble enzyme itself, which is a significant advantage in their prolonged use.

The invention is elucidated in detail by the aid of the following non-limiting Examples.

EXAMPLE 1

100.6 mg of Akrilex C-100 xerogel are suspended in 5.0 ml of a 0.1 molar potassium phosphate buffer (pH 7.0), and a solution of 102.5 mg of N-ethyl-N'-(3-dimethylaminopropyl)-carbodiimide hydrochloride in 2.5 ml of a cold (+4° C.) buffer solution is added to the suspension at 0° C. under steady stirring. After 10 minutes of stirring 47.4 mg of cholinesterase, dissolved in 2.5 ml of a cold (+4° C.) buffer solution, are added to the reaction mixture. The mixture is maintained at 0° to 4° C. for 48 hours; during this period the suspension is stirred twice for 6 hours, each. The gel is filtered off, washed thrice with 10 ml portions of a 0.1 molar potassium phosphate buffer (pH 7.0), thrice with 10 ml portions of a 0.1 molar potassium phosphate buffer (pH 7.0) also containing 0.5 moles of sodium chloride, and then thrice with 10 ml portions of a 0.1 molar potassium phosphate buffer (pH 7.0). Thereafter the gel is washed four times with 25 ml portions of distilled water, and the resulting salt-free gel is subjected to freeze-drying. 106.2 mg of an immobilized cholinesterase preparation are obtained. Activity: hydrolysis of 120 μmoles of butyryl-thiocholine iodide/min/g of dry substance.

EXAMPLE 2

102 mg of Akrilex C-100 xerogel are suspended in 5.0 ml of a 0.1 molar potassium phosphate buffer (pH 7.0), and a solution of 202 mg of N-cyclohexyl-N'-[β-(N-methylmorpholino)-ethyl]-carbodiimide p-toluenesulfonate in 2.5 ml of a cold (+4° C.) buffer is added to the suspension at 0° C. under steady stirring. After 10 minutes of stirring 49 mg of cholinesterase, dissolved in 2.5 ml of a cold (+4° C.) buffer solution, are added to the reaction mixture. The mixture is maintained at 0° to 4° C. for 48 hours; during this period the suspension is stirred twice for 6 hours, each. The gel is filtered off, washed thrice with 10 ml portions of a 0.1 molar potassium phosphate buffer (pH 7.0), thrice with 10 ml portions of a 0.1 molar potassium phosphate buffer (pH 7.0) also containing 0.5 moles of sodium chloride, and then thrice with 10 ml portions of a 0.1 molar potassium phosphate buffer (pH 7.0). Thereafter the gel is washed four times with 25 ml portions of distilled water, and the resulting salt-free gel is subjected to freeze-drying. 110 mg of an immobilized cholinesterase are obtained. Activity: hydrolysis of 110 μmoles of butyryl-thiocholine iodide/min/g of dry substance.

Comparative tests and results

The activity and specific activity of the immobilized enzyme preparations according to the invention were compared to the respective data of cholinesterase enzyme preparations immobilized on other supports. The following reference substances were applied:

(a) An Enzacryl AA type support (acryl amide—N,N'-methylene-bis-acrylamide copolymer containing aromatic amine functional groups, produced by Koch-Light Laboratories Ltd., Colnbrook, Bucks, Great Britain) was diazotized according to the prescriptions of the producer firm [Koch-Light Laboratories Ltd., KL 3, page 343 (1970)]. A mixture of 100 mg of the resulting diazotized Enzacryl AA support and 2.5 mg of cholinesterase was stirred in 0.5 ml of a 0.1 molar potassium phosphate buffer (pH 7.5) at 0°-4° C. for 8 hours, the suspension was allowed to stand in a refrigerator at 4° C. for 16 hours, then it was stirred again at 0°-4° C. for 8 hours, and kept again in a refrigerator at 4° C. for 16 hours.

(b) An Enzacryl AH type support [acryl amide-acrylic hydrazide—N,N'-methylene-bis(acryl amide)-copolymer, produced by Koch-Light Laboratories Ltd., Colnbrook, Bucks, Great Britain] was activated with sodium nitrite in acidic medium according to the prescriptions of the producer firm [Koch-Light Laboratories Ltd., KL 3, page 344 (1970)]. 100 mg of the activated support, which contains the functional groups in the form of acid azide groups, were admixed with 2.5 mg of cholinesterase enzyme in a 0.1 molar borate buffer (pH 8.0), and the resulting suspension was stirred under the conditions described in point (a) above.

(c) 93 mg of carboxymethyl cellulose with a binding capacity (—COOH content) of 2.3 meq/g, produced by Reanal Finomvegyszergyár, Budapest, Hungary, were suspended in 5 ml of a 0.1 molar potassium phosphate buffer (pH 7.0), and 50 mg of N-ethyl-N'-(3-dimethylaminopropyl)carbodiimide hydrochloride, dissolved in 2.5 ml of a cold (+4° C.) buffer solution, were added to the suspension under steady stirring. After 10 minutes of stirring 25 mg of cholinesterase, dissolved in 2.5 ml of a cold (+4° C.) buffer solution, were added to the suspension. The enzyme was reacted with the activated support at 0°–4° C. for 48 hours; during this time the mixture was stirred twice for 6 hours, each.

(d) A polymaleic anhydride support produced by the firm Merck (Darmstadt, German Federal Republic) was coupled with cholinesterase according to the prescriptions of the producer firm [Biochemics Merck: Poly(maleic anhydride) crosslinked enzyme support]. 1 g of the support was suspended in 25 ml of a 0.05 molar potassium phosphate buffer (pH 7.0) at 0° C., and after one minute of stirring 0.5 g of cholinesterase, dissolved in 5 ml of a cold (+4° C.) buffer solution, were added to the suspension. The pH of the reaction mixture was maintained between 8 and 9 by adding continuously a 1 n aqueous sodium hydroxide solution to the mixture. The introduction of the base was continued until the pH of the mixture remained constant for about 0.5 hours.

The immobilized enzyme preparations, obtained in the reactions described in points (a) to (d) above, were filtered off or centrifuged, and washed then with the buffer applied at immobilization, a 0.5–1.0 molar sodium chloride solution prepared with the same buffer, and then again with the buffer applied at immobilization, in order to remove the proteins not bound by covalent bonds. Thereafter the ions of the buffer solution were removed by washing the solids with water, and the immobilized enzyme preparations were subjected to freeze-drying. The freeze-dried products were stored in a refrigerator at 4° C.

The amounts of proteins bound in the immobilized enzyme preparations were determined indirectly, as the difference of the amount of protein introduced into the reaction mixture and remaining in the supernatant and wash after immobilization. The protein content of the cholinesterase solutions was determined by the biuret method [A. G. Gornell, C. S. Bardawill, M. M. David: J. Biol. Chem. 177, 751 (1949)].

The activity of dissolved and immobilized cholinesterases was determined by measuring the sulfhydryl groups liberated upon the decomposition of butyryl-thiocholine iodide substrate. The sulfhydryl groups were measured with bis(5-carboxy-4-nitrophenyl)-disulfide [G. L. Ellman, K. D. Courtney, V. Andres Jr., R. M. Featherstone: Biochem. Pharmacol. 7, 88 (1961)]. The amount of enzyme capable of catalyzing the conversion of 1 μmole of butyryl-thiocholine iodide per minute at 25° C. and at the optimum pH of the catalytic activity (pH 7.6 for the dissolved enzyme and 8.0 for the immobilized enzyme) was regarded as one activity unit.

The results of the tests are summarized in Table 1.

proaches that of the new product; polymaleic anhydride is, however, a support prepared by bulk polymerization, thus the throughflow characteristics of a column made of cholinesterase enzyme immobilized on polymaleic anhydride are much poorer than those of a column made of the product according to the invention, in which the enzyme is immobilized on polymer beads.

What we claim is:

1. An immobilized cholinesterase enzyme preparation, in which the cholinesterase enzyme is bound to a polymeric resin activated with a carbodiimide, said resin being built up from a first monomer selected from the group consisting of acrylic acid and methacrylic acid; a second monomer selected from the group consisting of acryl amide and methacryl amide; and a cross-linking agent selected from the group consisting of a compound having two acrylic moieties as terminal groups and a compound having two allyl moieties as terminal groups; and said polymeric resin containing at least 0.1 meq/g of —COOH functional groups.

2. A preparation as claimed in claim 1, in which the polymeric resin is in the form of beads.

3. A process for the preparation of an immobilized cholinesterase enzyme preparation, characterized in that a polymeric resin, built up from a first monomer selected from the group consisting of acrylic acid and methacrylic acid; a second monomer selected from the group consisting of acryl amide and methacryl amide; and a cross-linking agent selected from the group consisting of a compound having two acrylic moieties as terminal groups and a compound having two allyl moieties as terminal groups; and said polymeric resin containing at least 0.1 meq/g of —COOH functional groups, is treated with a carbodiimide derivative which is soluble in water or is soluble in an organic solvent at temperatures below 0° C., a solution of cholinesterase enzyme with a pH of 4.5 to 8.5 is applied to the resulting activated support, and the resulting product is washed.

4. A process as claimed in claim 3, characterized in that said polymeric resin contains 2 to 8 meq/g of —COOH functional groups.

5. A process as claimed in claim 3, characterized in that said resin is an Akrilex C polymer, prepared by the partial acidic or alkaline hydrolysis of Akrilex P acryl amide—N,N'-methylene bis(acryl amide)copolymer beads.

6. A process as claimed in claim 3, characterized in that cholinesterase is applied onto the activated support as a solution in a 0.1 molar potassium phosphate buffer (pH 7.0).

7. A process as claimed in claim 3, characterized in that cholinesterase is reacted with the activated support at 0°–4° C.

8. A process as claimed in claim 3, in which said resulting product is dried after said washing.

| Support | Immobilized protein, % | Immobilized activity, % | Activity recovered in dissolved state, % | Loss in activity, % | Activity of the product * | Specific activity, %** |
|---|---|---|---|---|---|---|
| Enzacryl AA | 100 | 0 | 0 | 100 | 0 | 0 |
| Enzacryl AH | 61.8 | 0.2 | 60.7 | 39.1 | 0.2 | 0.3 |
| Akrilex C-100 (Example 1) | 24.5 | 7.5 | 60 | 32.5 | 120 | 30.6 |
| Carboxymethyl cellulose | 5.5 | 0.2 | 3.5 | 96.3 | 2 | 3.6 |
| Polymaleic anhydride | 23.3 | 7.5 | 31.3 | 61.2 | 106 | 32.2 |

*unit/mg of dry substance
**the specific activity of the dissolved enzyme was regarded as 100%.

It appears from the data of Table 1 that the preparation according to the invention has the greatest activity related to both dry weight (protein + support) and protein content. The activity of the enzyme preparation immobilized on polymaleic anhydride support ap-